United States Patent [19]

Craig et al.

[11] Patent Number: Plant 7,620

[45] Date of Patent: Aug. 13, 1991

[54] REGAL PELARGONIUM NAMED 'FLAIR'

[75] Inventors: Richard Craig, State College, Pa.; Glenn G. Hanniford, Worthington, Ohio

[73] Assignee: Research Corporation Technologies, Inc., Tucson, Ariz.

[21] Appl. No.: 383,955

[22] Filed: Jul. 21, 1989

[51] Int. Cl.[5] ..... A01H 5/00

[52] U.S. Cl. ..... Plt./68

[58] Field of Search ..... Plt./68

*Primary Examiner*—Howard J. Locker

*Attorney, Agent, or Firm*—Scully, Scott, Murphy & Presser

[57] ABSTRACT

This invention relates to a new and distinct cultivar of regal Pelargonium (*Pelargonium*×*domesticum*) named Flair substantially as illustrated and described herein, particularly characterized as being compact and self-branching, early flowering and floriferous, and having flowers which are light orange-red in color with red-purple feathering primarily on the upper petals.

2 Drawing Sheets

The present invention relates to a new and distinct cultivar of regal Pelargonium (*Pelargonium*×*domesticum*) named Flair. This cultivar is characterized as being compact and self-branching (without pinching), early flowering and floriferous. The flowers are light orange-red with red-purple feathering primarily on the upper petals.

The cultivar was developed from an organized, scientifically designed breeding program conducted at the Department of Horticulture, The Pennsylvania State University, University Park, Pa. 16802. The objective was to produce a new regal Pelargonium genotype with excellent propagation characteristics, compact growth habit, predictable and consistent flowering response, and acceptable postharvest quality. The pedigree of this cultivar is as follows:

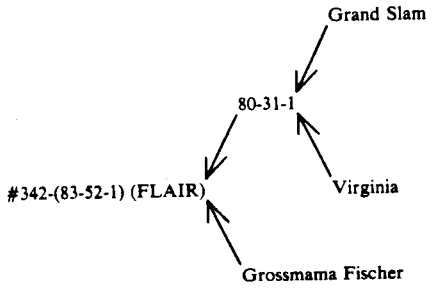

'Flair' has three cultivars in its ancestry: 'Grand Slam', 'Grossmama Fischer' and 'Virginia'. Flower color genes were derived from Grand Slam which is brick red and 'Grossmama Fischer' which has a strong orange salmon flower color. Neither of these cultivars flower well under warm temperature conditions. Flowering ability, earliness and heat tolerance of 'Flair' are similar to but not the same as that of 'Virginia'. The selection was asexually propagated by cuttings and the reproductions ran true.

Figure 1:
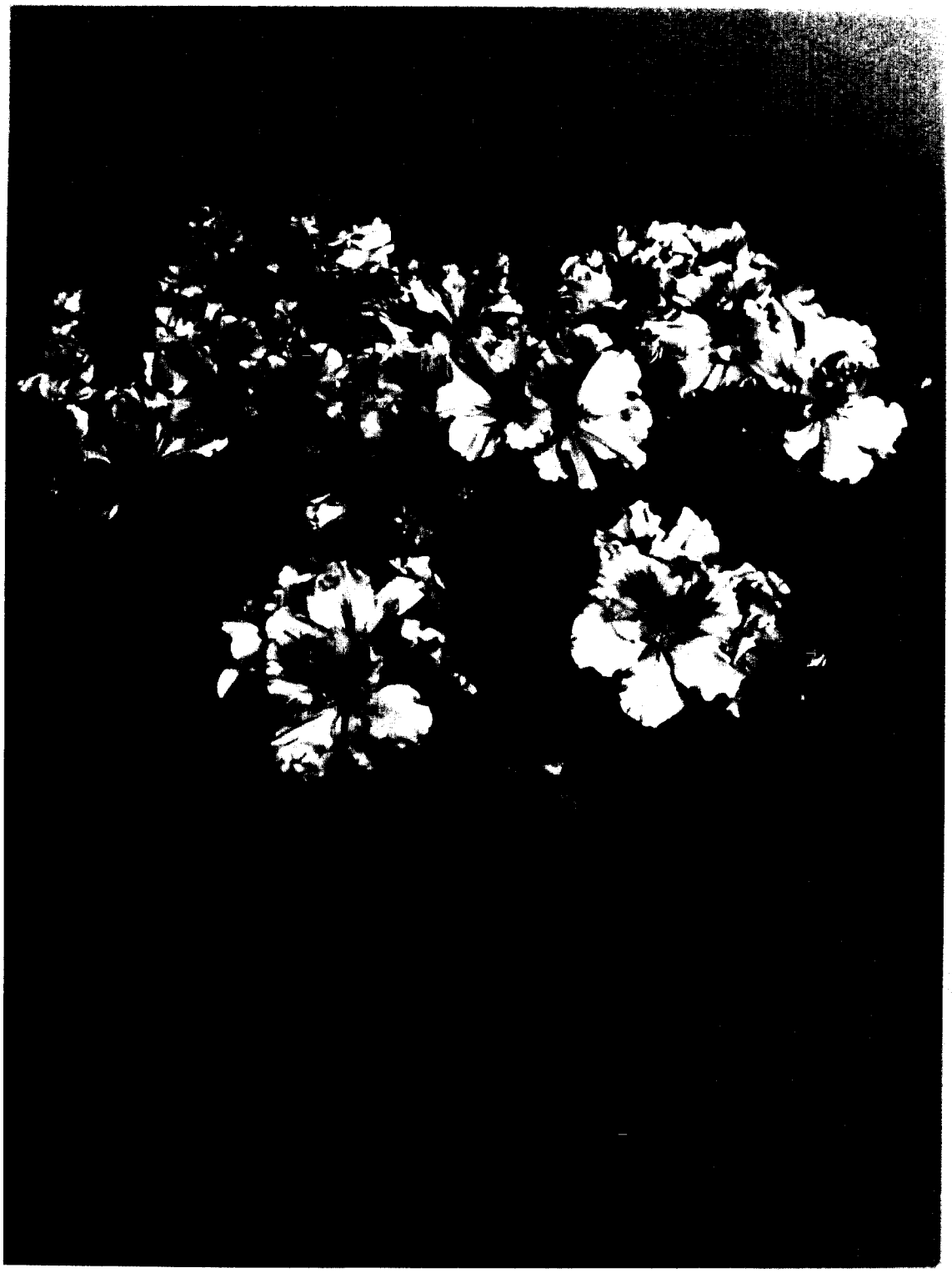
FIG. 1 illustrates in color the cultivar including foliage and flowers.
Figure 2:
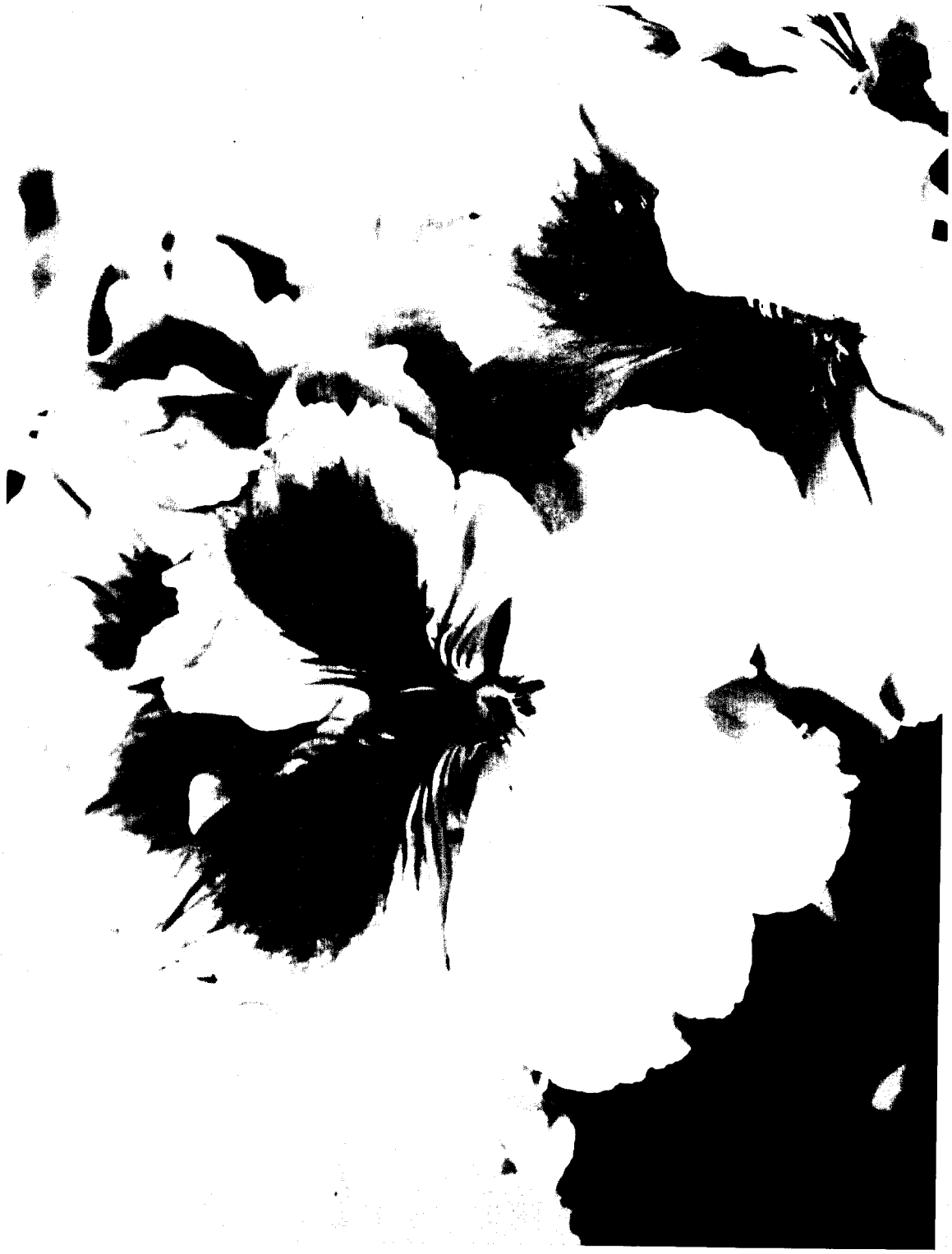
FIG. 2 illustrates in color primarily the floret.

With reference to the detailed description of the cultivar which follows, the test plant was potted in soilless medium and grown in a glasshouse under natural sunlight, at a night temperature of approximately 58° F. and a day temperature of approximately 68° F. Fertilizer was applied in every watering, with 200 ppm nitrogen provided in the forms of 15-16-17 (two consecutive waterings) and 20-0-20 (every third watering) in a repeating cycle.

Color readings were taken under incandescent light at approximately 200 foot candles and color identification was by reference to The Royal Horticultural Society Colour Charts, except where common terms of color definition are employed.

THE PLANT

Classification:

*Botanical.*—*Pelargonium*×*domesticum.*

*Tradename.*—Flair.

Form: Compact, self-branching.

Height: Approximately 14.5 cm to top of plant canopy (will vary with environmental and cultural conditions).

Leaves:

*Size.*—Largest leaf measured 9.0 cm long×11.5 cm wide.

*Shape.*—Depressed ovate; base is cuneate to truncate to reniform; variously lobed; ratio of length to width is 2 to 3.

*Margin.*—Toothed.

*Texture.*—Pubescent.

*Color.*—Adaxial: Green 137A. Abaxial: Yellow-green 144A.

*Ribs and veins.*—Palmate venation.

*Petioles.*—Texture: Lightly pubescent. Length: 9.0 to 11.0 cm. Color: Yellow-green 144A.

Stem:

*Internode length.*—1.5–3.0 cm.

*Color.*—Yellow-green 144A.

THE FLOWER

Blooming habit: Early and floriferous.

Inflorescence form: Umbellate.

Inflorescence size: Varies with floret number; often 8.0–11.0 cm across (with florets fully open).

Disease resistance: Not known.

Florets:

*Number.*—4 to 8 per inflorescence.

*Form.*—Cupped.

*Size.*—4.5–7.0 cm across open floret.

*Lasting quality.*—Good; comparable to the cultivar 'Olga'.

Petals:

*Number.*—5–6.

*Texture and appearance.*—Smooth.

*Color.*—Upper petals: Adaxial: Margin: Red 39B. Central spot: Greyed-purple 187A with orange-red 33B halo. Proximal veins and feathering: Red-purple 59A. Base: White 155D. Abaxial: Margin: Red 39B. Central spot: Greyed-purple 187A with orange-red 33A halo; slightly smaller than adaxial spot. Lower petals: Adaxial: Red 39B. Base: White 155D with infrequent light feathering greyed-purple 183B and orange-red 33A. Abaxial: Red 50C. Base: White 155A.

*Petaloids.*—Number: 0 to 1. Shape: Petal-like. Color: Similar to the color of the petals.

*Sepals.*—Number: 5–6.

*Pedicel.*—Subtended by bracts. Length: 1.7 to 3.3 cm. Color: Yellow-green 144A.

*Peduncle.*—Arises from node; opposed to leaf petiole; subtended by leaves and bracts. Length: 7.0 to 9.2 cm. Color: Yellow-green 144A.

Reproductive Organs

Androecium:

*Stamens.*—7–9 flat, ribbon-like filaments, joined at their bases; upper ⅓ of the filaments is pale purple; versatile attachment to anthers which are light purple and well developed; 2 sizes of orange pollen; anthers had a narrow extension at the tip of each anther.

*Staminodes.*—3–4 flat, ribbon-like filaments with no anthers.

*Petaloid stamens.*—None observed.

Gynoecium:

*Pistil number.*—1. Length: 11.5–16.0 mm. Stigma: 5–7-parted; purple. Style: 3.5–8.0 mm long; purple. Ovary: 4.0–5.0 mm long; superior; very pubescent.

*Fruit.*—Schizocarp; rarely observed.

What is claimed is:

1. A new and distinct cultivar of regal Pelargonium substantially as illustrated and described herein, particularly characterized as being compact and self-branching, early flowering and floriferous, and having flowers which are light orange-red in color with red-purple feathering primarily on the upper petals.

* * * * *

UNITED STATES PATENT AND TRADEMARK OFFICE

CERTIFICATE OF CORRECTION

PATENT NO. : Plant 7,620

DATED : August 13, 1991

INVENTOR(S) : Richard Craig, et al.

It is certified that error appears in the above-identified patent and that said Letters Patent is hereby corrected as shown below:

Column 3, line 19: "0 to 1" should read as --0 or 1--

Signed and Sealed this

Twenty-ninth Day of December, 1992

*Attest:*

DOUGLAS B. COMER

*Attesting Officer*

*Acting Commissioner of Patents and Trademarks*